US00PP16610P2

(12) United States Plant Patent
Hanes

(10) Patent No.: US PP16,610 P2
(45) Date of Patent: Jun. 6, 2006

(54) ***PETUNIA* PLANT NAMED 'WHIP REEDA'**

(50) Latin Name: *Petunia hybrida*
Varietal Denomination: Whip Reeda

(75) Inventor: Mitchell Eugene Hanes, Morgan Hill, CA (US)

(73) Assignee: Goldsmith Seeds, INC., Gilroy, CA (US)

( * ) Notice: Subject to any disclaimer, the term of this patent is extended or adjusted under 35 U.S.C. 154(b) by 119 days.

(21) Appl. No.: 11/094,750

(22) Filed: Mar. 31, 2005

(51) Int. Cl.
*A01H 5/00* (2006.01)

(52) U.S. Cl. ..... Plt./356
(58) Field of Classification Search ..... Plt./356

See application file for complete search history.

(56) References Cited

U.S. PATENT DOCUMENTS

PP14,136 P2 * 9/2003 Hirabayashi ..... Plt./356
PP14,159 P2 * 9/2003 Westhoff ..... Plt./356

OTHER PUBLICATIONS

UPOV ROM GTITM Computer Database, GTI Jouve Retrieval Software 2005/03 Citation for 'Whip Reeda'.*

* cited by examiner

*Primary Examiner*—Kent L. Bell
*Assistant Examiner*—W. C. Haas
(74) *Attorney, Agent, or Firm*—Jondle & Associates P.C.

(57) ABSTRACT

A *petunia* cultivar particularly distinguished by its large, red flowers and early flowering is disclosed.

1 Drawing Sheet

Figure 1:
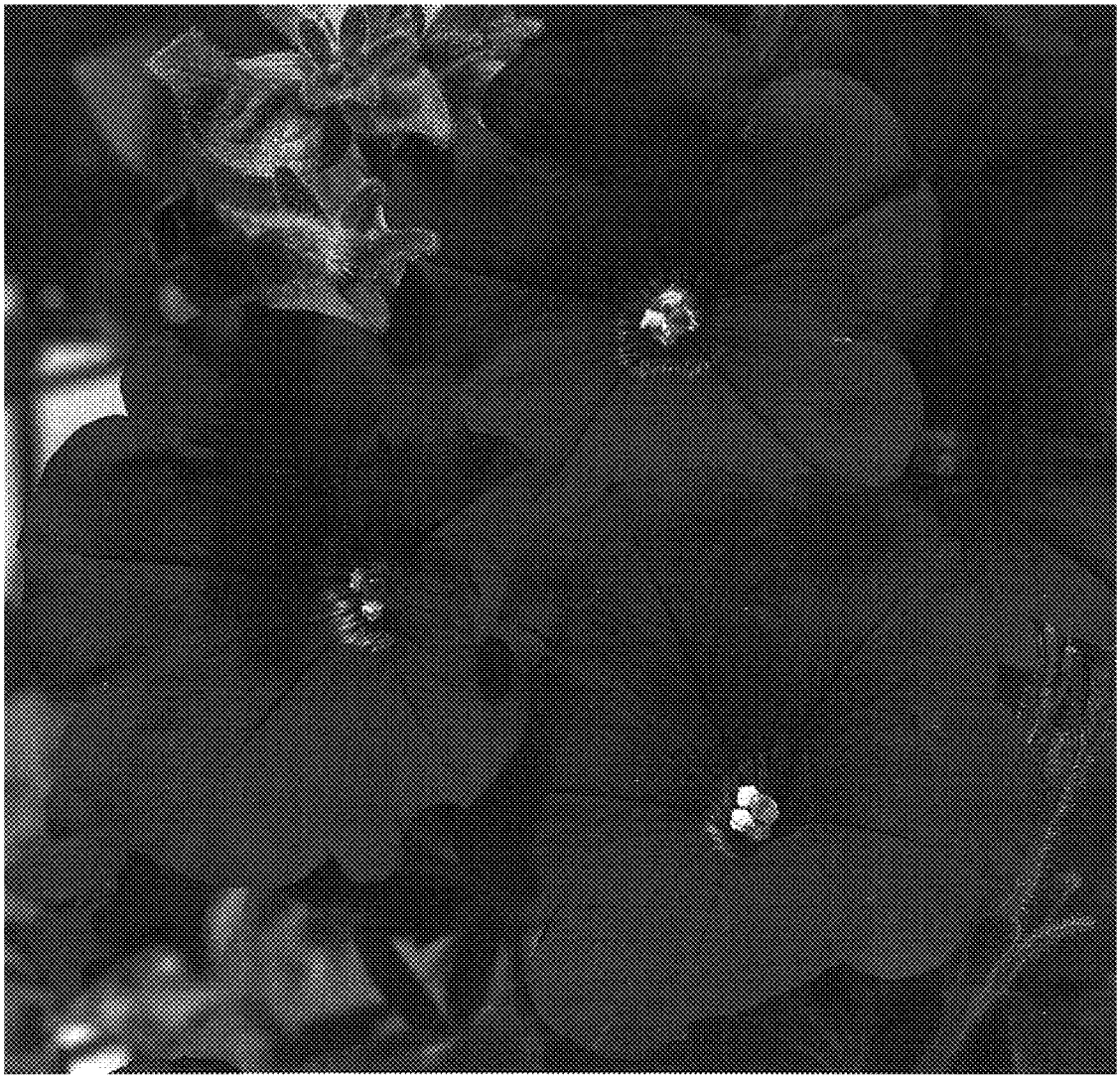

Genus and species: *Petunia hybrida.*
Variety denomination: 'Whip Reeda'.

BACKGROUND OF THE NEW PLANT

The present invention comprises a new and distinct cultivar of *petunia,* botanically known as *Petunia hybrida,* and hereinafter referred to by the cultivar name 'Whip Reeda'. The new cultivar originated from a hybridization made in the year 2001 in Gilroy, Calif. The female parent was '794-1', a red proprietary *petunia* line (unpatented), while the male parent was '785-1', a purple proprietary *petunia* line (unpatented).

The new cultivar was created as a single plant in 2001 in Gilroy, Calif. and has been asexually reproduced repeatedly by vegetative cuttings and tissue culture in Gilroy, Calif. and Andijk, The Netherlands over a two-and-a-half-year period. The plant has also been trialed at Gilroy, Calif., Litchfield, Mich. and Andijk, The Netherlands. The present invention has been found to retain its distinctive characteristics through successive asexual propagations.

DESCRIPTION OF PHOTOGRAPH

This new *petunia* plant is illustrated by the accompanying photograph which shows mature inflorescences; the colors shown are as true as can be reasonably obtained by conventional photographic procedures. The photograph is of a four-month-old plant grown in a lexan-covered greenhouse in a spring trial setting.

FIG. 1. The photograph shows mature inflorescences.

DESCRIPTION OF THE NEW CULTIVAR

The following detailed descriptions set forth the distinctive characteristics of 'Whip Reeda'. The data which define these characteristics were collected from asexual reproductions carried out in Gilroy, Calif. The plant history was taken on four-month-old plants grown in one-gallon pots in a poly-covered greenhouse. Color readings were taken in the greenhouse in the late winter season under natural light. Color references are primarily to The R.H.S. Colour Chart of The Royal Horticultural Society of London (R.H.S.) (2001 edition). Texture description details were observed under a dissecting microscope.

DETAILED BOTANICAL DESCRIPTION

Classification:
- *Botanical.*—*Petunia hybrida.*
- *Common name.*—*Petunia.*

Growth:
- *Growth and branching habit.*—Good vigorous habit, well-branched.
- *Form.*—Semi upright and decumbent.
- *Height.*—20.0 cm to 25.0 cm as measured from soil level, excluding blooms.
- *Width.*—30.0 cm to 35.0 cm excluding flowers.
- *Time to produce a finished flowering plant.*—8 to 11 weeks for a 4 to 6 inch pot.
- *Outdoor plant performance.*—Does well in full sun; used as a hanging plant, in mixed containers, patio containers.
- *Time to initiate and develop roots.*—18 to 23 days.
- *Root description.*—White, fibrous.

Leaves:
- *Arrangement.*—Alternate; upper leaves subalternate.
- *Immature leaf.*—Color: Upper surface: RHS 137A, but darker. Lower surface: RHS 137B. Length: 3.5 cm to 4.0 cm. Width: 2.5 cm to 3.5 cm.
- *Mature leaf.*—Color: Upper surface: RHS 137A. Lower surface: RHS 137B. Length: 4.5 cm to 5.0 cm. Width: 3.5 cm to 4.0 cm. Shape: Ovate. Margin: Entire. Apex: Obtuse. Base: Acuminate. Texture:

Glandular hairs. Venation: Palmate. Venation color: RHS 144B.

*Petioles.*—Length: 0.5 cm to 1.0 cm. Width: 0.4 cm. Color: RHS 144B. Texture: Hirsute, some glandular hairs.

Stems:

*Length.*—20.0 cm to 25.0 cm.

*Diameter.*—0.4 cm.

*Internode length.*—2.0 cm to 2.5 cm.

*Color.*—Closest to RHS 144A.

*Texture.*—Hirsute, some glandular hairs.

*Stem anthocyanin.*—None.

*Pedicel.*—Color: RHS 144A. Length: 2.5 cm to 3.0 cm. Diameter: 0.15 cm. Texture: Hirsute, some glandular hairs.

Flower buds:

*Shape.*—Oblong.

*Diameter.*—0.5 cm.

*Length.*—1.5 cm to 2.0 cm.

*Color when bud is first starting to open.*—RHS 182B.

Inflorescence:

*Blooming habit.*—Continuous throughout the growing season; good floriferousness.

*Lastingness of individual blooms.*—4 to 8 days.

*Fragrance.*—None.

*Inflorescence type.*—Flowers solitary in upper leaf axis.

*Floret type.*—Funnelform; 5 lobed petals, fused at base.

Flowers:

*Immature flower.*—Color: Upper side: Velvety RHS 46B, but deeper red. Color of main veins: RHS 187A. Color of secondary veins: RHS 183C. Underside: RHS 56C at the inner half of petals; RHS 51B at the outer half. Color of main veins: RHS N199A. Color of secondary veins: RHS 199A. Flower diameter: 3.7 cm to 4.0 cm.

*Mature flower.*—Color: Upper side: Closest to RHS 46B. Color of main veins: RHS 187B. Color of secondary veins: RHS 183D, but lighter shade. Underside: Closest to RHS 50D; wide band of RHS 54B at margin, but lighter shade. Flower diameter: 4.2 cm to 4.4 cm.

*Corolla.*—Color inside: RHS N155B; heavily overlaid with main veins of RHS 200A; Color of secondary veins: RHS 200B. Tube length: 2.6 cm to 2.9 cm. Texture: Hirsute; glandular hairs.

*Petals.*—Apex: Mucronulate. Base: Fused. Margin: Entire. Waviness: Weak. Lobation: Very moderate. Texture: Papillose.

*Calyx.*—5-lobed.

*Sepals.*—Number: 5, deeply lobed, fused at base. Color: RHS 137A. Length: 1.2 cm to 1.5 cm. Width: 0.3 cm to 0.4 cm. Shape: Oblong. Apex: Obtuse. Texture: Hirsute, many glandular hairs.

Reproductive organs:

*Stamens.*—Number: 5; 2 taller and 3 shorter. Filament color: RHS N155B. Filament length: 2.1 cm to 2.4 cm. Pollen color: RHS 11B.

*Pistil.*—Number: 1. Length: 3.0 cm to 3.1 cm. Stigma color: RHS 144B. Style color: RHS N145B.

*Fruit/seed set.*—Not observed.

Disease and insect resistance: Not observed.

COMPARISON WITH KNOWN CULTIVARS

'Whip Reeda' differs from the female parent '794-1' (unpatented) by having a more decumbent habit, shorter internodes and a brighter red flower than '794-1'. 'Whip Reeda' differs from the male parent '785-1' (unpatented) by having larger flowers, red flower color and earlier bloom time.

'Whip Reeda' differs from the commercial variety 'Keireom' (U.S. Plant Pat. No. 14,136) by having smaller elliptical-shaped foliage and a deeper red flower color with more color in the corolla.

I claim:

1. A new and distinct *petunia* plant as shown and described herein.

* * * * *